United States Patent [19]

Lee, Jr. et al.

[11] 3,969,499

[45] July 13, 1976

[54] DENTAL ADHESIVE MATERIALS CONTAINING FLUORIDE COMPOUNDS

[75] Inventors: Henry L. Lee, Jr., San Marino; Jan A. Orlowski, Altadena, both of Calif.

[73] Assignee: Lee Pharmaceuticals, South El Monte, Calif.

[22] Filed: Nov. 19, 1974

[21] Appl. No.: 525,048

Related U.S. Application Data

[63] Continuation of Ser. No. 146,466, May 24, 1971, abandoned.

[52] U.S. Cl. .................................... 424/52; 32/15
[51] Int. Cl.² ........................................ A61K 7/18
[58] Field of Search ................... 424/52, 15; 32/15

[56] References Cited
UNITED STATES PATENTS 3,427,366   2/1969   Verdol et al. ...................... 260/859

OTHER PUBLICATIONS

Galligan, et al. *J. of Dent. Res.*, vol. 47, No. 4, pp. 629–632, Aug. 1968.

*Primary Examiner*—Lewis Gotts
*Assistant Examiner*—Cary Owens
*Attorney, Agent, or Firm*—Irons & Sears

[57] ABSTRACT

A composition of matter comprising a polymeric reaction product of a hydroxy terminated butadiene prepolymer having an average molecular weight of about 400 to 25,000 and containing 1 to 3 hydroxyl groups per molecule and a polyisocyanate reactant present in an amount to provide from 100 to 1200 percent excess isocyanate groups to hydroxyl groups or active hydrogen sites, and from 1 to 70 percent by weight of a compound containing a fluoride ion. In another, and preferred aspect of the invention, the polyisocyanate reactant is present in an amount to provide from 1.5 to 2.7 isocyanate groups for each hydroxyl group or active hydrogen site, the composition containing an aromatic polyol, such as N,N-bis(2-hydroxypropyl) aniline, and wherein the aromatic polyol comprises at least 42 percent but not more than 60 percent of the hydroxyl components. The compositions are especially useful as dental fissure sealants and as means of applying a fluoride to a tooth surface.

14 Claims, No Drawings

DENTAL ADHESIVE MATERIALS CONTAINING FLUORIDE COMPOUNDS

BENEFIT OF PRIOR APPLICATION

This application is a continuation of application Ser. No. 146,466, filed May 24, 1971, and now abandoned.

BACKGROUND OF THE INVENTION

1. Field of the Invention

This invention relates in general to plastic films or membranes containing a medicament, which film or membrane is implanted in tissue or is adhered to tissue, bone, or tooth substrates. The plastic releases the medicament to the substrate over a period of time. In its more particular aspects, the invention concerns an improved polyurethane composition containing fluoride ion and the use of this composition as a dental fissure sealant which also serves as a topical fluoride treatment for the teeth.

2. Description of the Prior Art

In the past, polyurethane formulations based on polyether or polyester prepolymers have been utilized as cavity liners, i.e., resilient formulations interposed between the tooth surfaces and bulk restorative materials applied after removal of carious tissue. For example, U.S. Pat. No. 3,254,411 Shelly teaches such a liner prepared from a tetra-aromatic isocyanate.

An additional later teaching of polyurethanes generally in this art is Galligan et al., The Journal of Dental Research, 47, July–Aug. 1968, p. 629. Previously there has been difficulty with the initial bond strength being fugitive and the physical properties of such liners being degraded in vivo environment.

One approach which has been found to be successful in overcoming such difficulties with prior compositions in this art is to utilize a substantial excess of isocyanate reactant such as from 100 to 1200 percent based upon the available hydroxy groups reacted with the isocyanate group, and based upon the hydroxy reactant derived from a polybutadiene polyol. The handling characteristics of such compositions, however, have not been entirely satisfactory.

Tooth surfaces have been treated topically in the past with a fluoride ion through application of silicate cements containing compounds yielding fluoride ions. Although this process has been somewhat successful, silicate cements are not entirely satisfactory in their handling characteristics nor properties desirable for fissure sealants which require a thin nonporous adherent film resistant to peeling and cracking.

SUMMARY OF THE INVENTION

It has been discovered that polyurethane films or membranes containing a medicament such as a fluoride ion containing compound can be implanted in tissue or adhered to tissue, bone, or teeth and release the medicament to the substrate over a period of time. In a more specific aspect of the present invention a fluoride ion compound is incorporated into a particular polyurethane composition which can be utilized as an adhesive coating, cavity liner, or fissure sealant for teeth and that substantial amounts of fluoride ion can be released to the tooth structure therefrom in relatively short periods of time.

It has also been discovered that a specific polyurethane composition containing both aliphatic and aromatic polyols in specified ratios can be used as a greatly improved fissure sealant having excellent handling properties and which resists peeling from the tooth, and especially from fissures in the tooth surface. In this specific composition, the adhesive strength is relatively greater than the tear strength of the sealant film.

DESCRIPTION OF THE PREFERRED EMBODIMENTS

It has been found that a compound containing a fluoride ion may be added in amounts of from about 1 to about 70% by weight to a polyurethane composition comprised of a hydroxy terminated butadiene prepolymer having an average weight of about 400 to 25,000 and containing 1 to 3, preferably 2 hydroxy groups per molecule, and a polyisocyanate reactant present in a substantial excess ranging from 100 to 1200 percent based on the availability of active hydrogen sites when implanted in tissue, or adhering to tissue, bone, or tooth substrates, will release to the substrate significant amounts of fluoride ion in relatively short periods of time.

A particularly useful composition about 5 to 50% by weight of the fluoride compound in a polyurethane composition of the type described utilized as a dental adhesive or cavity liner or fissure sealant.

The polyisocyanate reactant may be any of the commercially available polyisocyanates especially diisocyanates. The di- or poly-functional character of the reactant is necessary for linear or crosslinking ability. Thus, materials such as diphenyl-methane 4,4'-diisocyanate dimer and trimer and blends of these in combination with monomer, the monomer itself, triphenylmethane triisocyanate, naphthalene 1,5-diisocyanate, tolylene diisocyanate, xylylene diisocyanate, diphenylether 4,4'-diisocyanate, bis(4-isocyanatocyclohexyl) methane, bis-1,4(2-isocyanatoethyl) cyclohexane, hydrogenated tolylene diisocyanate, isophorone diisocyanate, 2,2,4-trimethylhexamethylene diisocyanate, hexamethylene diisocyanate, hexamethylene diisocyanates biuret, bis(2-isocyanatoethyl) fumarate, linoleic acid dimer diisocyanate, etc., may be utilized.

The general reaction involved is set forth below. In the mouth, the isocyanate reacts with water to form unstable carbamic acid, which immediately decomposes, splitting off $CO_2$ to form the amine of the corresponding isocyanate. This amine reacts instantaneously with more isocyanate to further cross-link the adhesive through substitute urea groups.

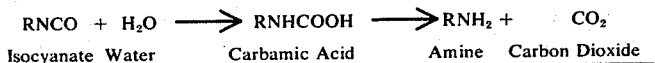

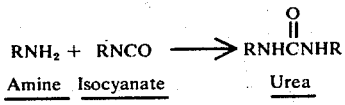

Examples of polymers of butadiene suitable in the practice of the invention include homopolymers such as polybutadiene and copolymers of butadiene with styrene (SBR) and acrylonitrile (NBR). In general, the average molecular weight of the reactant ranges from 400 to 25,000 and necessarily the reactant must be modified to provide hyroxy groups optimally present averaging 3 hydroxyl groups per molecule. A preferred molecular weight is from an average of about 750 to about 3000.

A preferred reactant is described as a prepolymer containing 1.8 predominantly primary, terminal, allylic hydroxyl groups per average molecule in a butadiene or modified butadiene polymer as in U.S. Pat. No. 3,427,366 Verdol et al. The subject matter of the Verdol patent above is incorporated by reference into this application with the exception that in the present invention for dental purposes a substantially greater excess of isocyanate is necessary with respect to the active hydrogen or hydroxyl or the diene intermediate polymer.

In order to achieve a desired coating thickness of from 1 to 50 microns, it is preferable that the reactants be applied to the tooth area from a solvent. The selection of the solvent is governed by the requirements that it facilitate any release by outgassing and that it has no active hydrogens which would react with the isocyanate groups. A preferred solvent is chloroform which has been found to achieve consistent film thicknesses of 5 to 15 microns. Other operable solvents include ketones such as acetone.

Any of the catalysts known to the art which are useful in isocyanate reactions may be used. A preferred catalyst is triethylenediamine, however, other examples such as dibutyltin, dilaurate butyltin trichloride and the like may be readily utilized.

Any compound containing fluoride in such form as to release fluoride ions may be added to the polyurethane compositions in amounts of 1 to 70% by weight. A preferred range is 5 to 50% of the fluoride ion containing compound. In the case of fissure sealants, about 5 to 15% by weight has been found particularly suitable for most situations. An especially useful amount for topical application of fluoride to the teeth is about 10% by weight of the solid in the resin composition.

Examples of fluoride containing compounds which may be used in the practice of this invention are: sodium fluoride, stannous fluoride, stannous hexafluorozirconate, calcium fluoride, disodium monofluorophosphate, the salt of n-hexadecylamine and hydrofluoric acid, the salt of oleylamine and hydrofluoric acid, magnesium silica fluoride, calcium silica fluoride, and potassium fluorophosphate.

As indicated, it has been found that a particularly useful polyurethane composition used by itself as a fissure sealant or with the fluoride additive described above possesses outstanding properties suitable for fissure sealants. This improved composition comprises a polymeric reaction product of a hydroxy terminated butadiene prepolymer having an average molecular weight of about 400 to 25,000 and containing 1 to 3 hydroxyl groups per molecule and a polyisocyanate reactant being present in an amount to provide from 1.5 to 2.7 isocyanate groups for each hydroxyl group or active hydrogen site, and an aromatic polyol, such as bis(hydroxypropyl) aniline, in an amount such that the ratio of the aromatic polyol to the aliphatic polyol is one where the aromatic diol comprises at least 42 and not more than 60% by weight of the polyols present.

It has been found that in formulating a suitable fissure sealant, that a flexible sealant which was coated onto the teeth and into the fissures would be ground off occlusal surfaces at the contact point during mastication and had a tendency to peel the sealant out of the fissures.

The particular composition described above is one which eventually breaks at points under mastication action but tends not to peel out of the fissures since the tear resistance in the film has been reduced to a value lower than the adhesive strength by building a more rigid backbone by the incorporation of the aromatic polyol which is reacted with the diisocyanate and which in turn is then reacted with an aliphatic polyol.

The ratios of components in the composition have been found to be critical since experience has shown that when the isocyanate to hydroxyl ratio drops to less than 1.5 to 1, the cure is less than satisfactory because the water on the tooth tends to use up most of the isocyanate, and the diol prepolymer is not cured into the system. If the isocyanate to hydroxy ratio exceeds 2.7 to 1, it has been found that the film is too brittle because of excess polyurea formed from the excess isocyanate. If the aromatic polyol makes up less than 42 percent of the polyols present, the film formed is so tough that it pulls out of fissures rather than breaking off. Where the aromatic polyol comprises more than 60 percent of the polyols present, the viscosity of the prepolymer solution is so low that the usual filler, pigments, and other such additives will not properly suspend in the composition.

In some cases, it has been found desirable to employ a finely divided filler such as titanium dioxide as a pigment and to facilitate solvent release. Also, silane keying or coupling agents capable of complexing with the inorganic elements in the tooth surface as well as reacting with the isocyanate groups may be employed as a formulation ingredient or applied to the tooth surface prior to coating with the sealant. A typical class of suitable materials is the silane containing non-tertiary amine groups, such as N-$\beta$-(aminoethyl)-$\gamma$-aminopropyltrimethoxy silane.

It has also been found advantageous to employ various acid pretreatments to the tooth surface before the application of the fissure sealant. Typically, the tooth surface is treated for about 1 minute with a 50% citric acid solution.

The following examples describing certain representative embodiments of this invention will serve to further illustrate the nature of this invention. Unless otherwise specified, the relationship of parts by weight to parts by volume is that of grams to cubic centimeters, and temperatures are degrees Centigrade.

EXAMPLE 1

17.25 parts of an aromatic polyisocyanate of a polybutadiene/acrylonitrile copolymer which is a liquid mixture of the monomer, dimer, and trimer forms, of 4,4'-diisocyanatodiphenylmethane, available commercially as Upjohn Isonate 143L, from the Upjohn Co., Polymer Chemicals Division, is added to a mixture of 23.4 parts of polybutadiene based diol (Hystil G-100 from Hystil Development Co.) having a molecuar weight of approximately 1,300, 2.32 parts of N,N-bis(2-hydroxypropyl) aniline, and 0.15 parts of triethylene diamine, in 150 parts of chloroform. The mixture is applied to tooth surfaces and is a very satisfactory fissure sealant.

EXAMPLE 2

The procedure of Example 1 is repeated but employing 18.15 parts of the isocyanate, 16.9 parts of the aliphatic diol and 2.38 parts of the aromatic diol. The ratio of isocyanate groups to hydroxy groups is 2.5 to 1. A tough adherent film is formed when this composition is applied to tooth surfaces.

EXAMPLE 3

The procedure of Example 1 is repeated but employing 18.14 parts of the isocyanate, 16.3 parts of the aliphatic diol, and 2.86 parts of the aromatic diol. The ratio of isocyanate groups to hydroxy groups is 2.44 to 1.

EXAMPLE 4

A composition comprising 90 parts solids of the resin formulation of Example 3 to which are added 10 parts by weight of disodium monofluorophosphate is applied to prepare tooth substrates as follows:

The occlusal surfaces of teeth are cleaned and made free of deposits, and rinsed thoroughly with a water spray and dried. A 50 percent solution of citric acid is applied to the dried surfaces with a cotton pellet or swab and the acid solution allowed to remain in contact with the tooth surfaces for 1 minute, after which the teeth are thoroughly rinsed with a water spray. The teeth are then air-dried. The above composition is then applied to the tooth in a thin film and dried with a gentle stream of air for 3 minutes.

The procedure of this example may be followed and 0.5 parts of N-β-(aminoethyl)-γ-aminopropyltrimethoxysilane incorporated in the composition. Alternatively the tooth surface to be coated can be treated first with a solution of hydrolyzed vinyl triacetoxy silane to increase adhesion of the fissure sealant.

EXAMPLE 5

To 90 parts solids of the resin formulation of Example 3, 10 parts of disodium monofluorophosphate powder are added with stirring. The resulting mixture is then spread as a thin film on each of three aluminum dishes which are treated with a silicone wax release agent. The films are cured at room temperature for 24 hours and then stripped from the aluminum dish. The average thickness of each sample is 6 mil and the weight is 300 mg. The samples are placed in polypropylene beakers and covered with 50 cc of distilled water. A Beckman pH meter fitted with an Orion Research specific ion electrode is employed to measure fluoride ion release rates from the sample. The electrode is calibrated to standard solutions of disodium monofluorophosphate as controls. After each measurement, the water is poured off and each container rinsed with 50 cc of distilled water and an additional 50 cc of fresh distilled water is added. The amount of fluoride ion in the water is a measure of the loss of fluoride from the sealant film. In the first 24 hours, 8 parts per million fluoride is released; after 33 days, 0.75 parts per million is lost in a 24 hour period. Summation of the daily losses over a 33 day period accounted for 25 mg out of a possible 30 mg in the average sample. Measurement of tensile strengths of the samples compared to the samples prepared without the addition of disodium monofluorophosphate indicates that there is no significant difference in the tensile strength caused by the addition of the disodium monofluorophosphate. From the foregoing tests, it is concluded that the release of the disodium monofluorophosphate from the resin binder film of the present invention releases at least 80 percent of the available fluorine within the first month.

EXAMPLE 6

The formulation employed in Example 4 is applied as films to the bottoms of polypropylene beakers and allowed to cool at room temperature for approximately 1 hour. Thereafter 100 mg samples of powdered bovine enamel are sprinkled across the bottom of each beaker and 15 cc of distilled water added. At the end of 4 days standing at room temperature, the water is poured off, the beaker rinsed thoroughly with 25 cc distilled water, and the rinse added to the retained water from the experiment. The water containing the enamel is then filtered in Whatman Co. no. 3 filters and the filters air-dried overnight. 60 mg of pre-treated powder of each sample is then exposed to 0.4 molar acetic acid, buffered to a pH of 3.8 for 3 hours. Thereafter the samples are washed with 10 cc distilled water and dried three hours at 52°C to constant weight, and then dried under a vacuum. Controls of enamel in uncoated polypropylene beakers are treated in a similar fashion. Typical weight losses are as follows: the loss of the 300 mg control sample is 58.1 mg, and the weight loss for enamel in contact with 10% by weight disodium monofluorophosphate is 31.3 mg, a 46.7 percent reduction in the weight loss, indicating that exposure to the disodium monofluorophosphate film has a hardening effect on the enamel.

EXAMPLE 7

Three groups of Sprague-Dawley albino rats weighing 65 to 78 grams and 30 to 35 days of age are treated as follows:

Group I — The animals are anesthetized and the upper molars ground with a dental bur to blunt all occlusal surfaces. Three days later the animals are again anesthetized and the sealant film described in Example 4 applied as follows: the molar teeth are washed and air dried, then washed with a 50% citric acid solution and a 1 minute etching time permitted. The molars are washed, air-dried, and then coated with a single application of the sealant of Example 4 by means of a cotton applicator and air-dried for two minutes. The last step is repeated with the control animals, that is, the teeth are etched with a citric acid solution with no subsequent sealant applied. The experimental and control groups are then placed on NIDR Diet 2000 (Nutritional Biochemicals Company) 1 hour after application of the sealant.

A culture of *Streptococcus mutans*, NIDR 6715-12 is introduced by eye dropper into the mouth of both experimental and control animals. An additional amount of the culture is introduced into deionized drinking water. Feces from infected rats are also added to the water supply. The rats are kept on the contaminated water for three days. Only deionized water is used for the first two weeks postoperatively, then tap water containing less than 1 ppm fluoride is given. Fluoride activity is determined by means of a fluoride ion electrode. The electrode is attached to a Beckman pH meter.

Group II — A second group of experimental control rats is treated in a similar manner except that the molars are not rounded down with a dental bur.

Group III — Procedure employed with Group I is repeated except that the teeth are not rounded nor the animals innoculated with the bacteria.

After 46 days of being on Diet 2000, the animals are sacrificed and the upper and lower jaws removed and the molars washed and placed in a sonic cleaning device. The teeth fixed in a solution of 80 parts of absolute alcohol and 20 parts of 10 percent neutral aqueous formaldehyde. The presence of carious lesions is determined, the examination being conducted blind, that is, the examiner is not told whether each jaw inspected belongs to experimental or control animals. The results are indicated in the Table below.

TABULATION OF CARIOUS LESIONS*

| Group No. | No. of Animals | Treatment | Innoculation Strain | No. of Lesions Max.** | Mand.*** |
|---|---|---|---|---|---|
| I | 20 | Upper molars ground Coated with sealant | NIDR 6715-12 | 3 | 5 |
| I | 20 | Upper molars ground Uncoated | NIDR 6715-12 | 7 | 18 |
| II | 20 | Coated with sealant | NIDR 6715-12 | 12 | 24 |
| II | 20 | Uncoated | NIDR 6715-12 | 24 | 32 |
| III | 5 | Coated with sealant | Not innoculated | 0 | 1 |
| III | 5 | Uncoated | Not innoculated | 0 | 0 |

*Determined according to Sognnaes, R.F., Experimental Rat Caries, Location, Sequence and Extent of Carious Lesions Produced in the Norway Rat When Raised on a Generally Adequate, Finely Powdered Purified Ration, J. Nutr. 39: 139, 1949; and Van Reen, R. and Cotton, W.R. In Art and Science of Dental Caries Research, pg. 287, (R.S. Harris, Ed.), Academic Press, New York and London, 1968.
**Max. — Maxillary Molars.
***Mand. — Mandibular Molars.

From the Table, it is apparent that in Group I there was a 68 percent reduction in the incidence of caries in the treated teeth. There was a 29 percent reduction in Group II. In Group III, there is one lesion found in the treated teeth and none in the control animals.

What is claimed is:

1. A composition of matter comprising a polymeric reaction product of a hydroxy terminated butadiene prepolymer having an average molecular weight of about 400 to 25,000 and containing 1 to 3 hydroxyl groups per molecule and a polyisocyanate reactant present in an amount to provide from 1.5 to 2.7 isocyanate groups for each hydroxyl group or active hydrogen site, and from 1 to 70% by weight of a fluoride ion containing compound capable of releasing fluoride ion.

2. A composition of matter as claimed in claim 1 wherein said fluoride ion compound is present in the amount of 5 to 50% by weight of the composition.

3. A composition of matter as claimed in claim 1 wherein said fluoride ion compound is disodium monofluorophosphate.

4. A composition of matter as claimed in claim 3 wherein about 5 to 15% of disodium monofluorophosphate is present.

5. A composition of matter as claimed in claim 3 wherein about 10% of disodium monofluorophosphate is present.

6. A composition of matter comprising a polymeric reaction product of a hydroxy terminated butadiene prepolymer having an average molecular weight of about 400 to 25,000 and containing 1 to 3 hydroxyl groups per molecule and a polyisocyanate reactant present in an amount to provide from 1.5 to 2.7 isocyanate groups for each hydroxyl group or active hydrogen site, and an aromatic polyol, wherein the aromatic polyol comprises at least 42 but not more than 60 percent of the hydroxyl components.

7. A composition of matter as claimed in claim 6 further comprising from 1 to 70% by weight of a fluoride ion containing compound capable of releasing fluoride ion.

8. A composition of matter as claimed in claim 6 wherein the aromatic polyol is N,N-bis(2-hydroxypropyl) aniline.

9. A composition of matter as claimed in claim 6 containing a silane coupling agent.

10. A composition of matter as claimed in claim 7 wherein said fluoride ion compound is present in the amount of 5 to 50% by weight of the composition.

11. A composition of matter as claimed in claim 7 wherein said fluoride ion compound is disodium monofluorophosphate.

12. A composition of matter as claimed in claim 11 wherein about 5 to 15% of disodium monofluorophosphate is present.

13. A composition of matter as claimed in claim 11 wherein about 10% of disodium monofluorophosphate is present.

14. A composition as claimed in claim 12 wherein the aromatic polyol is N,N-bis(2-hydroxypropyl)aniline.

* * * * *